US008535680B2

(12) United States Patent
Colombo et al.

(10) Patent No.: US 8,535,680 B2
(45) Date of Patent: Sep. 17, 2013

(54) **ANTI-LPS FACTOR FROM *PARIETARIA JUDAICA* AND METHODS OF USE THEREOF**

(75) Inventors: Paolo Colombo, Palermo (IT); Angela Bonura, Partinico (IT); Francesco Di Blasi, Palermo (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 218 days.

(21) Appl. No.: 12/933,390

(22) PCT Filed: Mar. 19, 2009

(86) PCT No.: PCT/EP2009/053238
§ 371 (c)(1),
(2), (4) Date: Oct. 12, 2010

(87) PCT Pub. No.: WO2009/115568
PCT Pub. Date: Sep. 24, 2009

(65) Prior Publication Data
US 2011/0045010 A1    Feb. 24, 2011

(30) Foreign Application Priority Data
Mar. 19, 2008    (IT) .............................. PA2008A0007

(51) Int. Cl.
*A61K 38/00*    (2006.01)
*A61K 39/00*    (2006.01)
*C07K 1/00*    (2006.01)
*C07K 2/00*    (2006.01)

(52) U.S. Cl.
USPC .......... 424/185.1; 514/1.1; 530/300; 530/350

(58) Field of Classification Search
None
See application file for complete search history.

(56) References Cited

U.S. PATENT DOCUMENTS

| | | | | |
|---|---|---|---|---|
| 6,090,388 | A * | 7/2000 | Wang ......................... | 424/185.1 |
| 7,265,208 | B2 * | 9/2007 | Saxon et al. ............... | 530/387.1 |
| 2005/0031631 | A1 | 2/2005 | Geraci et al. | |
| 2006/0155116 | A1 | 7/2006 | Costa et al. | |
| 2007/0178122 | A1 | 8/2007 | Geraci | |

FOREIGN PATENT DOCUMENTS

| | | |
|---|---|---|
| WO | 00/44781 | 8/2000 |
| WO | 02/20790 | 3/2002 |
| WO | 2004/104047 | 12/2004 |
| WO | 2005/085278 | 9/2005 |

OTHER PUBLICATIONS

Bonura et al. "A hybrid expressing genetically engineered major allergens of the *Parietaria* pollen as a tool for specific allergy vaccination" Int. Arch. Allergy Immunol. 142:274-284 (2007).
Bonura et al. "Hypoallergenic variants of the *Parietaria judaica* major allergen Par j 1: A member of the non-specific lipid transfer protein plant family" Intl. Arch. Allergy Immunol. 126:32-40 (2001).
Colombo et al. "Identification of an immunodominant IgE epitope of the *Parietaria judaica* major allergen" J. Immun. 160:2780-2785 (1998).
Costa et al. "cDNA cloning, expression and primary structure of Par j 1, a major allergen of *Parietaria judaica* pollen" FEBS Lett. 341:182-186 (1994).
Duro et al. "cDNA cloning, sequence analysis and allergological characterization of Par j 2.0101, a new major allergen of the *Parietaria judaica* pollen" FASEB Lett. 399:295-298 (1996).
Ferreira et al. "Modulation of IgE reactivity of allergens by side-directed mutagenesis: Potential use of hypoallergenic variants for immunotherapy" FASEB J. 12:231-242 (1998).
Goldsby et al. *Immunology* 5$^{th}$ *Ed*. W.H. Freeman & Co., pp. 62-67 (2002).
Menna et al. "Characterization of a dodecapeptide containing a dominant epitope of Par j 1 and Par o 1, the major allergens of *P. judaica* and *P. officinalis* pollen" Allergy 54:1048-1057 (1999).
Miyazaki et al. "Intracellular transport blockage caused by disruption of the disulfide bridge in the third external domain of major histocompatibility complex class I antigen" Proc. Natl. Acad. Sci. USA 83:757-761 (1986).
Olsson et al. "Contribution of disulphide bonds to antigenicity of Lep d 2, the major allergen of the dust mite *Lepidoglyphus destructor*" Mol. Immun. 35:1017-1023 (1998).
Pastorello et al. "Lipid transfer proteins and 2S albumins as allergens" Allergy 56 (Suppl 67):45-47 (2001).
Polo et al. "Studies on the relationship between structure and IgE-binding ability of *Parietaria judaica* allergen I" Mol. Immunol. 28:169-175 (1991).
Smith & Chapman "Reduction in IgE binding to allergen variants generated by site-directed mutagenesis: Contribution of disulfide bonds to the antigenic structure of the major house dust mite allergen Der p 2" Mol. Immunol. 33:399-405 (1996).
Stryker *Biochemistry* 4$^{th}$ *Ed*. W.H. Freeman & Co., pp. 35-39 (1995).
Andrä et al. "Mechanisms of endotoxin neutralization by synthetic cationic compounds" *Journal of Endotoxin Research*, vol. 12, No. 5, pp. 261-277 (Jan. 2005).
Colombo et al. "The Allergens of *Parietaria*" *International Archives of Allergy and Immunology*, vol. 130, No. 3, pp. 173-179 (Mar. 2003).
Duro et al. "Isolation and characterization of two cDNA clones coding for isoforms of the *Parietaria judaica* major allergen Par J 1.0101"*International Archives of Allergy and Immunology*, vol. 112 No. 4, pp. 348-355 (Jan. 1997).
Pristovšek & Kidrič "Peptides neutralizing lipopolysaccharide—Structure and function" *Mini Rev. Med. Chem.*, vol. 1, No. 4, pp. 409-416 (Nov. 2001).
Lin et al. "Lipopolysaccharide neutralization by the antibacterial peptide CM4" *European Journal of Pharmacology*, vol. 596, Nos. 1-3, pp. 160-165 (Oct. 2008).
Li et al. "The molecular mechanism of interaction between sushi peptide and *Pseudomonas* endotoxin" *Cellular & Molecular Immunology*, vol. 3, No. 1, pp. 21-28 (Feb. 2006).

(Continued)

*Primary Examiner* — Albert Navarro
(74) *Attorney, Agent, or Firm* — Nixon & Vanderhye PC

(57) ABSTRACT

The present invention falls within the field of molecular biology, and in particular it refers to peptides, polypeptides, protein molecules, uses, methods, processes, systems and compositions for minimizing the presence of molecules in a material and/or interfering with effects associated to such molecules. In particular, the present invention can appear in the form of anti-septic shock pharmacological composition and systems of purification from bacterial endotoxins.

20 Claims, 9 Drawing Sheets

(56) References Cited

OTHER PUBLICATIONS

Zhang et al. "Neutralization of endotoxin in vitro and in vivo by a human lactoferrin-derived peptide" *Infection and Immunity*, vol. 67, No. 3, pp. 1353-1358 (Mar. 1999).

Int'l Search Report for PCT/EP2009/053238, nine pages, mailed Jul. 10, 2009.

Written Opinion for PCT/EP2009/053238, eight pages, mailed Jul. 10, 2009.

\* cited by examiner

```
SEQ ID NO 38
AntiLPS 38
1                                                                64
QETCGTMVRALMPCLPFVQGKEKEPSKGCCSGAKRLDGETKTGPQRVHACECIQTAMKTYSDID
65                                                              128
GKLVSEVPKHCGIVDSKLPPIDVNMDCKTVGVVPRQPQLPVSLRHGPVTGPSDPAHKARLERPQ
129       139
IRVPPPAPEKA

P43217 / NLT11_ParJ1.01

SEQ ID NO 42
AntiLPS 42
1                                                                64
EEACGKVVQDIMPCLHFVKGEEKEPSKECCSGTKKLSEEVKTTEQKREACKCIVRATKGISGIK
                            103
NELVAEVPKKCDIKTT-LPPITADFDCSKIQSTIFRGYY P55958/NLT21_Parj1.02
```

Figure 1

SEQ ID NO 41
AntiLPS 41
1                                                                                  37
LPVSLRHGPVTGPSDPAHKARLERPQIRVPPPAPEKA Parj1.01 C-terminal peptide 37

Figure 2

LAL TEST

| Amount of protein | Parj1.01 | Parj1.02 |
|---|---|---|
| 1 μg | + | + |
| ½ | + | + |
| ¼ | + | - |
| 1/8 | + | - |
| 1/16 | + | - |
| 1/32 | + | - |
| 1/64 | + | - |
| 1/128 | + | - |
| 1/256 | + | - |

Figure 3

EMOCYTE CYTOTOXICITY

| Stimulus | Concentration of the Par37 peptide | O.D. (415 nm) |
|---|---|---|
| 1XPBS | | 0,041 |
| Par37 | 2,5 µM | 0,044 |
| | 25 µM | 0,041 |
| | 250 µM | 0,041 |
| | 2,5 mM | 0,045 |
| | 25 mM | 0,040 |
| Triton X100 | 0,1% | 3,3 |

Figure 6

ANTI-LPS FACTOR FROM *PARIETARIA JUDAICA* AND METHODS OF USE THEREOF

This application is the U.S. national phase of International Application No. PCT/EP2009/053238, filed 19 Mar. 2009, which designated the U.S. and claims priority to Italy Application No. PA2008A000007 filed 19 Mar. 2008; the entire contents of each of which are hereby incorporated by reference.

STATE OF THE ART

Endotoxin is a microbial toxin, integral part of the outer membrane of the cell wall of Gram-negative bacteria, which is completely released with bacterial lysis. It consists of sub-molecular units ranging in size between 10.000 and 20.000 Daltons, whereas aggregations have sizes of about 100.000 Daltons. Unlike exotoxins, endotoxins are not secreted outside by bacteria, but are internal structural components thereof, which can spread in the host organism following death of the bacterium itself (above all by lysis). A typical example of endotoxin is represented by the lipopolysaccharide (LPS), which is present in the outer membrane of Gram-negative bacteria. Endotoxins are in large part responsible of the clinical consequences of infections with Gram-negative bacteria, as in the case of fulminant meningitis. In fact, endotoxin is held responsible for pathogenesis of sepsis, septic shock and the entailed multiorgan failure (MOF). Owing to its particularly aggressive and multi-factor nature, sepsis rapidly leads to death and constitutes the main cause of decease in non-coronary intensive therapies worldwide, with death rates of from 20% for sepsis to 40% for severe sepsis, to over 60% for septic shock: overall, in the world every day about 1400 persons die by sepsis. Hence the need, for the treatment of sepsis, to remove and/or deactivate endotoxins from the patient's body before the disease degenerates. With regard to endotoxin presence in the blood, a complex immunobiological activation is triggered that involves several biological systems (immune and reticuloendothelial) and an array of mediators, mainly freed by activation of macrophages, monocytes and other cells. Until endotoxin continues to stimulate the above-described mechanism, with the entailed triggering of inflammatory response, there is the risk of degenerating into a septic process. Moreover, endotoxins are frequent contaminants of plasmid DNA extracted from bacteria, and of all those products that are extracted and/or came into contact therewith. Endotoxins have to be removed from these products in order to prevent inflammatory reactions during in vivo applications, such as, e.g., gene therapy. In pharmaceutical preparations, it is necessary to remove all endotoxin traces that may affect the production process, because even small amounts might cause toxic-type clinical effects in patients treated with contaminated products.

Proteins capable of binding components of the bacterial wall are reported in literature. They have a molecular weight ranging between 2 and 80 kDa and contain positively charged amino acids (hence, the term "cationic proteins").

Moreover proteins denominated non-specific Lipid Transfer Proteins (ns-LTPs) are also known. They are small protein molecules of approximately 10 KDa that demonstrate high stability, and are usually present in all vegetal organisms studied to date. Such proteins are characterized by their ability to transport lipid molecules through membranes in vitro, though recent studies showed that they seem to exhibit a protective function, as able to act as peptides having antimicrobial activity. In several vegetal species they have been identified as allergens, as in the case of the Rosaceae Prunoideae (peach, apricot, plum), and Pomoideae (apple) and in the Urticaceae like *Parietaria*. Recombinant DNA technology allowed the isolation of various allergens of the ns-LTPs family, among them those of *Parietaria* denominated Parj1 and Parj2 (Colombo, P., et al., The allergens of *Parietaria* Int Arch Allergy Immunol. 2003 March; 130(3): 173-9, Review). In particular, to date two Parj1 allergen isoforms have been isolated, denominated (according to International nomenclature) Parj1.01 and Par1.02 (Costa et al. cDNA cloning, expression and primary structure of Par jI, a major allergen of *Parietaria judaica* pollen. FEBS Lett., 1994 Mar. 21; 341 (2-3):182-6; Duro et al., Isolation and characterization of two cDNA clones coding for isoforms of the *Parietaria judaica* major allergen Parj 1.0101, International Archives of Allergy and Immunology 1997 April; 112(4): 348-55). Such isoforms essentially differ due to the presence of a 37-aa Carboxy-terminal region exclusively present in Parj1.01 isoform (see FIG. 1 for details).

Scope of the present invention is to provide new means for the treatment and diagnosis of pathological conditions due to bacterial endotoxins.

SUMMARY OF THE INVENTION

The present invention is based on the unexpected discovery that a portion of *Parietaria judaica* major allergen, Parj1.01, has the characteristic of acting as a peptide or a protein capable of binding components of the bacterial membrane, such as the lipopolysaccharides (PLS) of endotoxins. The binding properties of these proteins and peptides involve important therapeutic and diagnostic aspects.

Accordingly, a first object of the invention is an isolated peptide capable of binding and/or neutralizing the biological activity of a component of bacterial membrane, such as a lipopolysaccharides (LPS) endotoxin, said peptide having the sequence $[X'-(aa)_n-X'']_m$. In a specific embodiment of the invention the peptide is a hybrid protein comprising the region $(aa)_n$ and a heterologous protein, wherein the region $(aa)_n$ is at the amino-terminal end of, or at the carboxy-terminal end of, or inserted inside the heterologous protein. In another embodiment of the invention the peptide is in multimeric form.

Further objects of the invention are all tools necessary for producing the peptides as an expression product in a modified host cell, namely nucleic acids coding for the peptides of the invention, expression or cloning systems comprising such nucleic acids operatively linked to expression control, promotion and/or regulation sequences, host cells transformed by means of the expression or cloning systems.

Still further objects of the invention are the claimed peptides for use in a method of medical and/or diagnostic treatment, specifically in a method of treatment or diagnose of sepsis and inflammatory reactions or as an immunosuppressive adjuvant in therapy.

Other objects are compositions comprising the peptide of the invention and pharmaceutically acceptable excipient, adjuvants or diluents and methods for their preparation.

Still other objects are medical devices comprising the peptide of the invention for use in binding, removing or deactivating LPS endotoxins, in particular for preventing or treating septic shock or inflammatory reactions.

Specific objects are medical device wherein the peptide is comprised in a purifying unit suitable for extra-corporal treatment of body fluids and in vitro methods for interfering and/or minimizing the biological effects associated to presence of LPS in a liquid or in a biological material.

DESCRIPTION OF THE FIGURES

FIG. 1: The figure shows the amino acid sequences of Parj1.01 and Parj1.02.

The sequence according to the main embodiment of the invention is indicated by boldface and underlined.

FIG. 2: Amino acid sequence of Par37 peptide. The amino acid sequence is expressed by using the one-letter code.

FIG. 3: Values related to endotoxin concentration of solutions containing Parj1.01 and Parj.02 after incubation with LPS (*Escherichia coli*, serotype 026:B6). The values were obtained by the kit Multi-test *Limulus Amebocyte* Lysate (LAL) pyrogen plus test (Bio-Whittaker, USA) sensitivity 0.12 EU. + and − indicate presence/absence of clots in the solution containing the two allergens. Left-hand column indicates dilutions of proteins used for the test.

Figure 4:
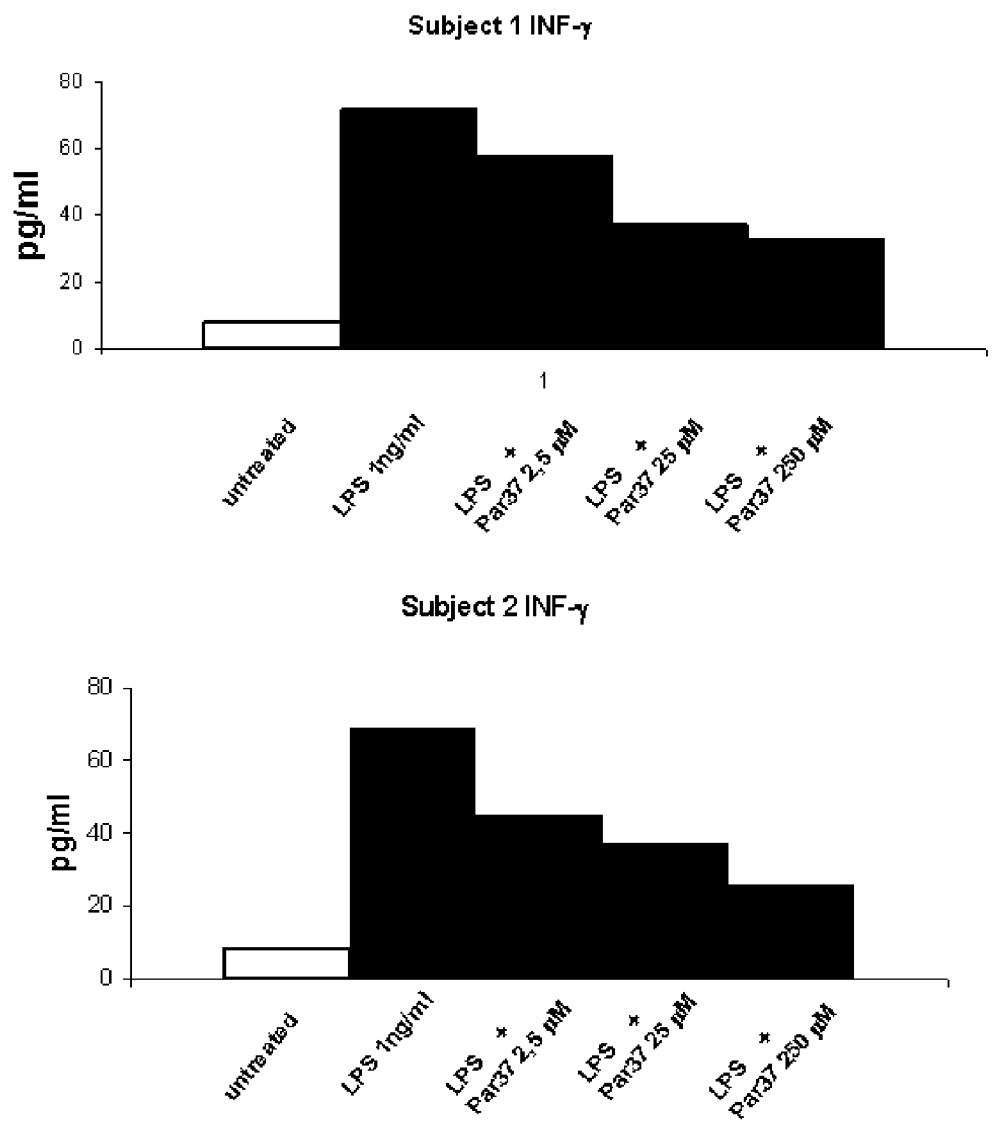

FIG. 4: ELISA Test of INF-γ cytokine release inhibition by PBMC of non-allergic subjects after stimulation with LPS and pre-incubated LPS, with increasing concentrations of the Par37 synthetic peptide. The values on the x-axis indicate the relative concentrations of antigens used. Values on the y-axis indicate cytokine picograms released in response to the treatments. Black bars indicate values relative to stimulated samples, white bars indicate untreated control samples.

Figure 5:
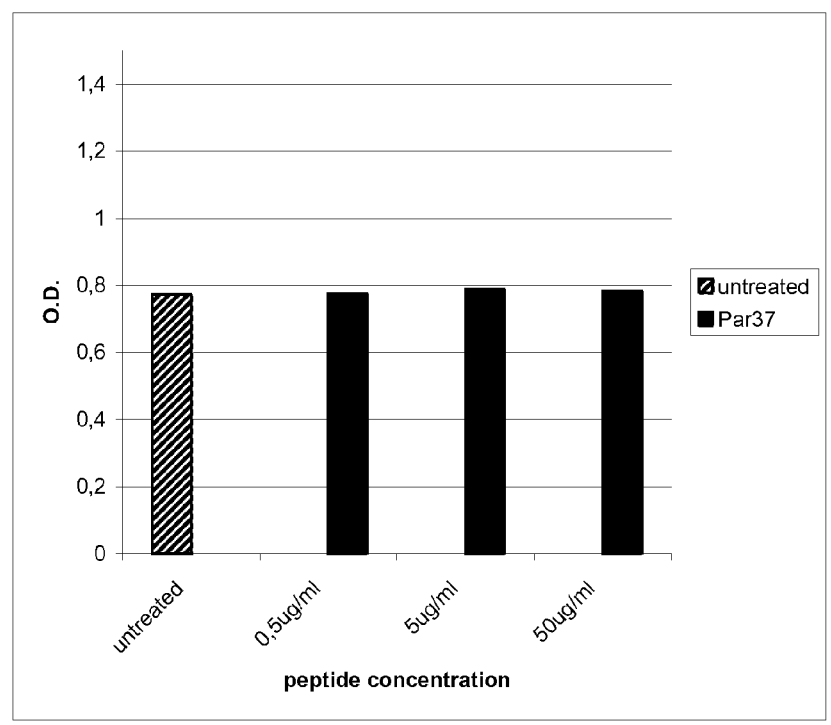

FIG. 5: Cytotoxicity test carried out with HeLa cells in culture. The assay describes the bioreduction of MTS (Owen's Reagent) produced by enzymes having dehydrogenase activity present in metabolically active cells. Values on the x-axis indicate the concentration of antigen used for the test, whereas values on the y-axis indicate the absorbance of the solutions indicated at a 490 nm wavelength.

FIG. 6: Hemolysis test with human erythrocytes. The assay is capable of describing possible hemolysis induced after incubation with Par37 peptide at different concentrations. There were used 1×PBS as negative control and 0.1% Triton X100 as positive control. Optical Densities measured at 451 nm indicate hemoglobin release in the medium following cell lysis.

Figure 7:
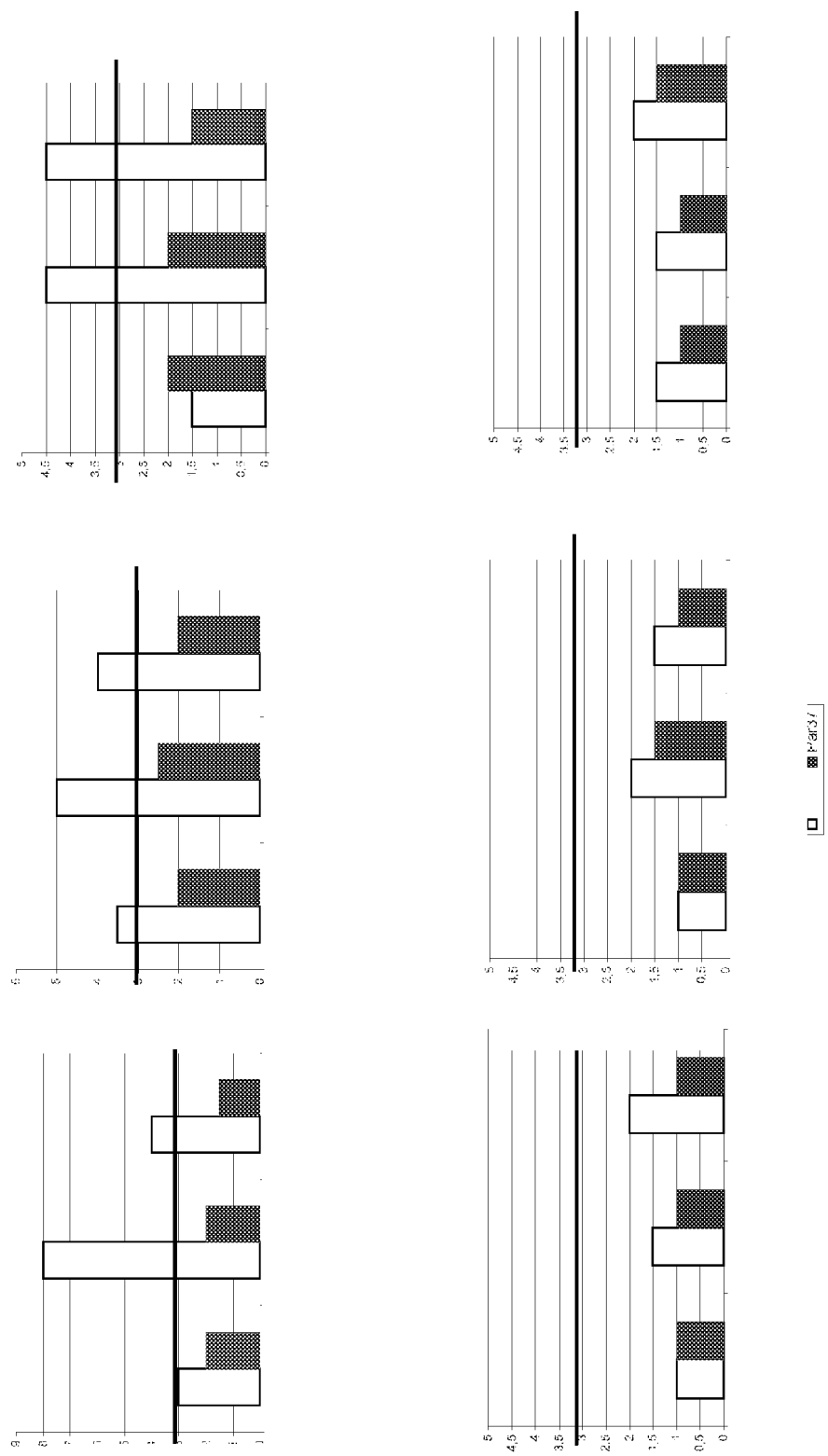

FIG. 7: Analysis of PBMC proliferation of 3 Pj allergic patients and 3 healthy subjects. Stimulation was conducted by adding to the culture medium rParj1 and Par37 synthetic peptide at a concentration of 0.1, 1 and 10 μg/ml. Numerical values on the y-axis indicate proliferation indexes with respect to the unstimulated sample. White histograms identify PBMC stimulated by Parj1, black histograms identify PBMC stimulated by Par37 peptide. Horizontal bars indicate significance values (values above the bar indicate a positive stimulation; values below the bar indicate absence of proliferation).

Figure 8:
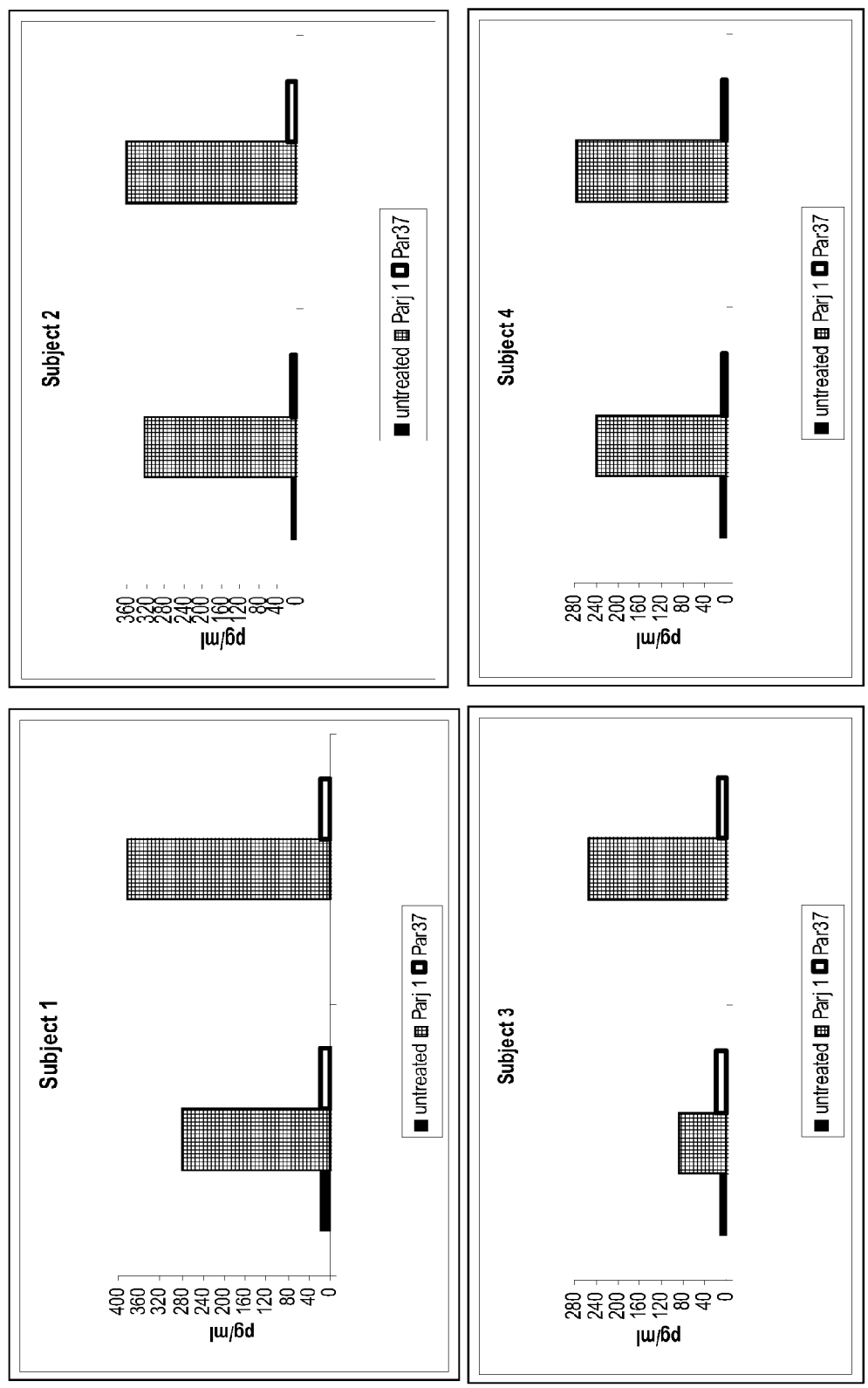

FIG. 8: ELISA Test of IFN-γ cytokine release from PBMC of non-allergic subjects. Values reported on the x-axis indicate the concentration of antigens used (1 and 10 μg/ml) whereas values on the y-axis indicate cytokine picograms released in the culture medium. Black bars indicate the values of the unstimulated sample (negative control), checkered bars the values of cells stimulated by rParj1.01, white bars the values obtained from cells stimulated by Par37 peptide.

Figure 9:
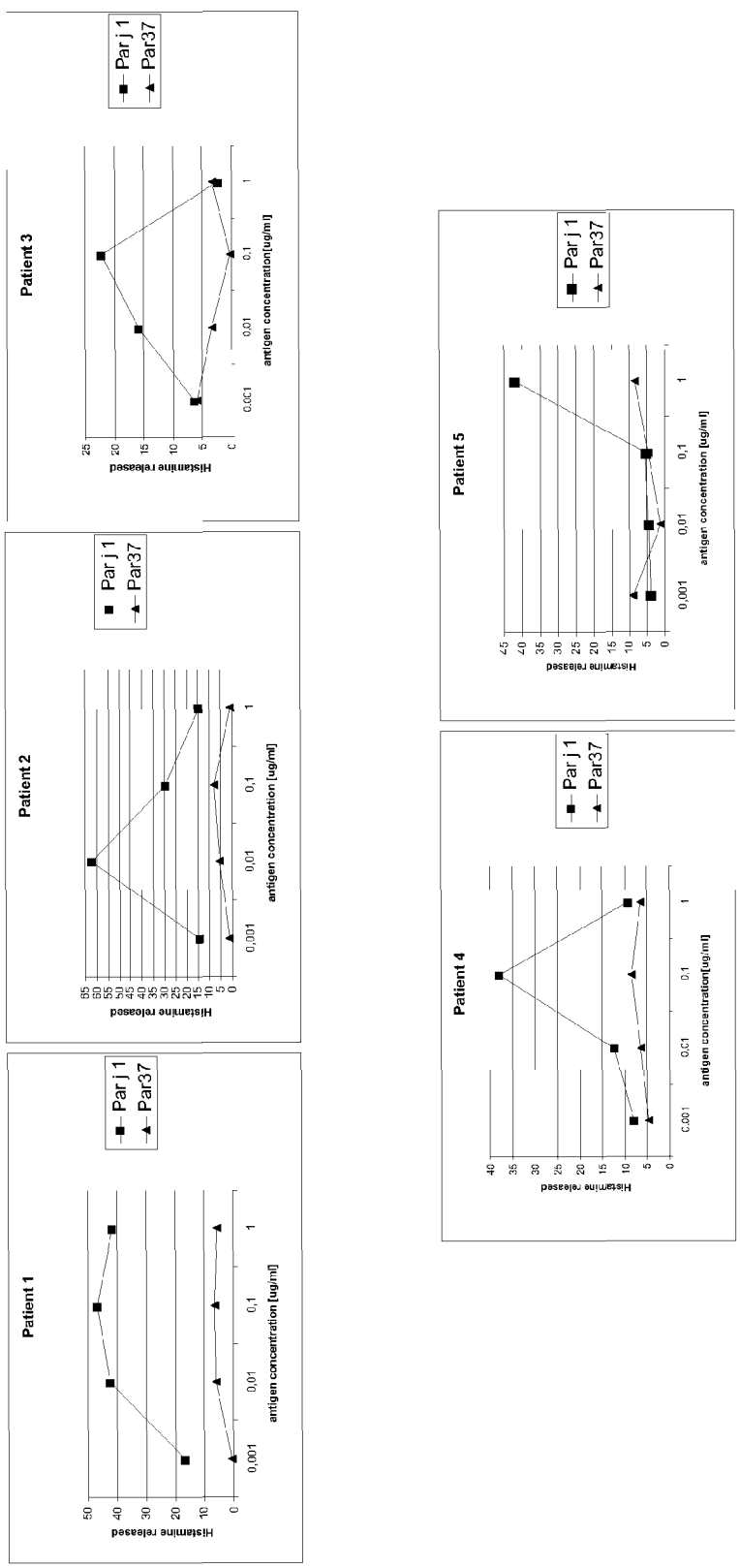

FIG. 9: Testing of histamine release from blood of Pj allergic patients. The antigens used were: rParj1 (line with squares, denominated Pj1) and the Par37 peptide (line with triangles). On the x-axis the amounts of protein used, and on the y-axis the percentage of histamine released with respect to the percentage of total histamine present in the patient's mastocytes are reported.

DETAILED DESCRIPTION

The present invention relates to some proteins of plant origin or peptides capable of binding components of the bacterial cell membrane, among which LPS. One of these protein is an allergen of the ns-LTP family of *Parietaria* denominated.

Sequence analyses have shown that the isoform Parj1.01 has the characteristic of having a size (139 aa) uncommon with respect to other nsLTPs isolated from various vegetal species, for instance those available under the EMBL ACCESSION NUMBERS: □40454, Q40453, Q2PCE0, Q9M5C1, Q2PCB9, A2ZAS9, A9NP97, A9NKX9, Q2PCD9, Q0WYX3, Q2PCD7, P27056, Q8WO0R7, Q8LK72, O24037, Q2XX08, A7Q4WO0, Q5NE30 or Q2XX25.

The best alignment among these proteins may be carried out using blast algorithm: NCBI BLAST program reference Altschul S. F., Madden T. L., Schäffer A. A., Zhang J., Zhang Z., Miller W., Lipman D. J. Gapped BLAST and PSI-BLAST: A New Generation Of Protein Database Search Programs. Nucleic Acids Res. 25:3389-3402 (1997).

An analysis on silica, conducted by the algorithm made available by Antimicrobial Peptide database (http://aps.unmc.edu/AP/main.php), highlighted that the carboxy-terminal portion of Parj1 (from amino acid 103 to 139, hereinafter defined as Par37 peptide) has peculiar characteristics.

The data reported in FIGS. 1 and 2 describe the origin, and characteristics of such carboxy-terminal portion of Parj1.01 allergen.

This peptide (see FIG. 2) has a total net positive charge of +5, a high percentage of 24% of proline residues, hydrophobicity percentage of 29% and a molecular weight of 3972.57 Dalton, that may suggest the reason why this peptide exhibits the capability of functioning as an antimicrobial agent, capable of binding Gram-negative bacteria cell wall components, such as lipopolysaccharide.

These characteristics are extended also to all peptides derived from the native sequence of Par37 as described in the present application, having the characteristic of interfering with the immunological mechanisms induced by bacterial membrane components during sepsis-associated phenomena.

Accordingly, the invention relates to peptides in isolated form whose sequence has a homology of at least 60%, but preferably at least 70% or 80% or 90% or 95% or 99% or even 100%, with the sequence of Par37 (SEQ ID NO: 41) and having net positive charge.

For peptide having a "net positive charge" is meant any peptide wherein the number of basic amino acid residues, susceptible of being positively charged, exceeds the number of acid amino acid residues.

The isolated peptides of the invention are represented by the following general formula (I):

$$[X'-(aa)_n-X'']_m \quad \text{Formula (I)}$$

wherein aa means any amino acid residue, m is an integer from 1 to 100, the region $(aa)_n$ is a peptide having from 10 to 37 amino acid residues and having a total net positive charge and X' and X'' are each independently a linear peptide from 0 to 1000 amino acid residues.

The region $(aa)_n$ is the peptide sequence LPVSLRHGPVT-GPSDPAHKARLERPQIRVPPPAPEKA (SEQ ID NO:41) or any derivative thereof obtained by substitution of any amino acid residue by a residue having equivalent charge characteristics or by deletion of up to 27 residues, provided that the total net charge remains positive.

In particular, derivative of the above indicated peptide SEQ ID NO:41, are analogs peptides having sequences originated by single or multiple amino acid substitutions on suitable sites capable of optimizing the neutralizing ability of the analogs. Such peptides can include the entire 37-aa sequence or fragments of smaller size. The derivative peptides can derive from amino-terminal, carboxy-terminal, internal deletion and/or substitution of amino acid residues in any combination according to what is reported hereinafter, in a manner such as to maintain a positive net charge of the peptide. Substitutions of the natural sequence with amino acids having similar charge are to be considered as equivalent, and therefore defined as conservative substitutions. In fact, a possible subdivision among amino acids is represented by the type of side chain: aliphatic (Glycine, alanine, valine, leucine, isoleucine), containing hydroxyl or sulphide (Serine, cysteine, threonine, methionine), aromatic (Phenylalanine, tyrosine, tryptophan), Basic (Histidine, lysine, arginine), acidic (Aspartic acid, glutamic acid, asparagine, glutamine) and cyclic (proline). Or, a further subdivision depending on the amino acid charge: "positively charged amino acid" can include Lys (lysine), Arg (arginine) and His (Histidine). "Polar uncharged" amino acid, comprising Gly (glycine), Gln (glutamine), Asn (asparagine), Ser (serine), Thr (threonine), Tyr (tyrosine). "Non-polar amino acids" can include Leu (leucine), Ile (isoleucine), Phe (phenylalanine), Ala (alanine), Val (valine), Pro (proline), Met (methionine), Trp (tryptophan), and Cys (cysteine). In general, all classifications reported in textbooks and therefore of easy access for any operator in the field.

A specific embodiment of the present invention is a peptide having the following structured: X'-aa1-aa2-aan-aa36-aa37-X", wherein X' and X" are, independently one from the other, a linear chain consisting of 0 to 4 amino acids and the sequence comprised between X' and X" is any sequence functional equivalent to that between aa1 and aa37 of SEQ ID NO:41. This specific peptide may also be modified to obtain a cyclic configuration.

Another specific embodiment of the invention is an hybrid peptide or fusion proteins comprising the region $(aa)_n$ of formula (I) and a heterologous protein, wherein the region $(aa)_n$ is fused either at the amino-terminal end of the heterologous protein or at its carboxy-terminal end or inserted inside the heterologous protein. Constructs of this type may be prepared by genetic engineering techniques and/or chemical cross-linking techniques.

Still another embodiment of the invention consists of a multimer protein having sequence of formula (I) wherein the index m is an integer higher than 1, preferably it is 2, 5, 10, 20 or 100. According to this embodiment, X' and X" may consist of 0 amino acid residues. In this case the multimer peptide comprises a multimer form of SEQ ID NO:41 or of any derivative thereof as described above. Alternatively, X' and X" may consist of 1, 2 or so many residues to form an heterologous protein. In this case the multimer peptide comprises a multimer form of an hybrid protein.

Specific examples of the peptide of the invention is SEQ ID NO:41 and its substitution derivatives containing 37 amino acid residues: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30 and SEQ ID NO:31.

Example of deletion derivatives are peptide of sequence: SEQ ID NO:32, SEQ ID NO:33, SEQ ID NO:34, SEQ ID NO:35, SEQ ID NO:36 and SEQ ID NO:37.

Examples of fusion peptides are peptide of sequence: SEQ ID NO:39 and SEQ ID NO:40.

The preparation of all peptides of the invention may be carried out according to synthetic methods, either in homogeneous or in heterogeneous phase, all well known to those skilled in the art. Alternatively, the different peptides are produced by expression in modified host cells according to known recombinant DNA technologies, employing usual cloning and expressing vectors and suitable host cells, all tools well known and available to those skilled in the art.

In particular, the polynucleotide DNA sequence coding for the *Parietaria judaica* allergen Parj1 was described in the earlier application WO-A-02/020790, whereas hybrid proteins comprising the allergen Parj1 are described in the earlier application WO-A-2005/085278, both herein incorporated by reference.

Substitution derivatives of the carboxy-terminal region of this allergen may easily be obtained by site specific mutagenesis technology and purification techniques also well known to those skilled in the art. See for example WO-A-02/020790 (examples 1, 2 and 3).

The present invention relates to molecules, methods, uses, processes and systems comprising or involving peptides capable of binding components of the bacterial membrane such as, e.g. lipopolysaccharide (LPS) and/or capable of interfering with, and in particular minimizing, the effects associated to LPS and to other components of the bacterial membrane, like, e.g., toxic effects on living beings, and specifically on human beings and animals. Because of these properties, the claimed peptides are efficient, inexpensive and safe antimicrobial agents neutralizing the biological activity of components of the bacterial membranes, as showed by the experimental work described in the application.

The data reported in FIG. 3 demonstrate that Par37 peptide is capable of binding bacterial endotoxin even when laying inside a molecule of greater size (Parj1.01 protein). In particular, FIG. 3 describes the capability of two native isoforms (Parj1.01 and Parj1.02) of major allergen Parj1 of binding LPS of bacterial origin. The data shown in FIG. 3 highlight how exclusively the isoform containing the Par37 peptide (Parj1.01) has the LPS-binding capability. This characteristic can entail relevant therapeutic implications, as demonstrated hereinafter. These examples are understood to be also for all peptides, polypeptides and protein molecules comprising the Par37 peptide and its derivatives described above.

FIG. 4 shows an experiment of IFN-γ secretion from human PBMC after stimulation with LPS. From this figure it is inferred that LPS administration to peripheral blood cells has as effect a powerful release of IFN-γ proinflammatory cytokine. On the other hand, pre-treatment of the LPS-containing sample with increasing doses of a synthetic peptide having the sequence of Par37 peptide has as effect a dramatic reduction of IFN-γ release from these cells.

Moreover, cytotoxicity tests conducted on cells in culture (Hela cell lines) (FIG. 5) and with erythrocytes of human origin (FIG. 6) demonstrated that this molecule has no toxic effect on analyzed cells. Therefore, the decreased release of cytokine by human PBMC is not a consequence of a toxic activity of the peptide, but of its capability of binding LPS, subtracting it from the binding with its receptor, present on the cells having the antigen, decreasing the inflammatory response. In order to better understand the immunological activity of the Par37 synthetic peptide, there were carried out studies capable of assessing the immunological activity of the molecule described in the invention by lymphocyte stimulation and IFN-γ release assays. As it is inferred from FIG. 7, it was observed that Par37 peptide is not capable of inducing lymphocyte proliferation both in Pj allergic patients (n=3) (who had an evident response to the whole Parj1.01 molecule) and in non-allergic subjects (n=3). Likewise, when PBMC from healthy subjects (n=4) were studied for their ability to release IFN-γ cytokine in response to Parj1.01 antigen, an impressive secretion of cytokine was observed in the sample stimulated with the whole allergen. On the other hand, samples stimulated with Par37 synthetic peptide exhibited very low cytokine production, equivalent to the (untreated) control sample (FIG. 8). Lastly, in consideration of the fact that this peptide derives from a molecule having allergenic activity, the anaphylactic activity of Par37 synthetic peptide was studied. FIG. 9 shows histamine release experiments carried out on blood of subjects allergic to *Parietaria* pollen (n=5). This assay demonstrated that this peptide has no anaphylactic activity. To sum up, the data reported by the present inventors highlighted that Par37 peptide has the characteristic of strongly binding the bacterial endotoxin, decreasing the release of pro-inflammatory cytokines and having no toxic effect.

The data reported herein show the medical applications of the peptides of the invention and of its derivatives, as well as the pharmaceutical compositions comprising the synthetically produced protein and methods of preparation of the pharmaceutical compositions. Pharmaceutical compositions suitable in the administration of the molecule of the invention are in the form of aqueous, hydroalcoholic or oily solutions, of emulsions or suspensions, in aqueous or oily medium, or of liposome suspensions. Besides the described formulations in liquid form, the compositions of the invention can be in semi-solid form like creams, pomades, gels or other forms suitable for topical application. Implants for subcutaneous application aimed at a prolonged release may be used as well. The compositions according to one of the aspects of the invention are formulated for a parenteral administration, in subcutaneous, intramuscular or intravenous use, for a topical administration on the skin or mucosae or for oral administration. Moreover, the compositions according to one aspect of the invention can be formulated for the preparation of systems of purification from LPS. An exemplary non-limitative application is represented by hemoperfusion columns which enclose therein the peptide or its derivatives removing endotoxins from the bloodstream and, anyhow, any extracorporeal system for the purification of components of the bacterial membranes. A further application is that related to the use of this peptide and/or derivatives thereof as adjuvant in immunosuppressive therapy in any embodiment comprising the peptide and/or derivatives.

The invention will be illustrated in some of its aspects by means of specific examples concerning the experimental steps of the preparation and the assessment of the immunological properties of the Par37 molecule as a representative peptide. These examples have a merely illustrative purpose, in no way being limitative of the invention.

EXAMPLE 1

Production of Recombinant Proteins and Assays for Determination of Endogenous Endotoxin Amount The recombinant proteins used in this description were prepared according to what described in the work by Bonura et al. A hybrid expressing genetically engineered major allergens of the *Parietaria* pollen as a tool for Specific Allergy Vaccination Int Arch Allergy Immunol 2007; 142(4):274-84. The values related to endotoxin concentration of the solutions were obtained by the *Limulus Amebocyte* Lysate (LAL) Multi-test pyrogen plus test kit (Bio-Whittaker, USA), 0.12 EU sensitivity.

For this test, Parj1.01 and Parj1.02 preparations with an endotoxin concentration equal to 0.125 EU/μg protein were used. In particular, two HisTrap™ HP columns (GE Healthcare) were loaded with 100 μg of Parj1.01 and Parj1.02 following the manufacturer's instructions.

Then, on the same columns 100 μg LPS (from *Escherichia coli*, 026:B6 serotype, SIGMA, UK) were passed. After repeated washings, proteins were eluted as described above and dialyzed against PBS1X for 24 h in order to obtain the samples in a buffer compatible with LAL testing. Before the assay, protein concentration was again determined by using the Bradford method.

LAL test was carried out on eluted fractions, in order to evaluate endotoxin concentration present in the samples. The results are reported in FIG. 3; the sample coming from the column on which Parj1.01+LPS were loaded exhibits a positive reaction to the endotoxin down to a ¹⁄₂₅₆ dilution, unlike the result obtained with the sample Parj1.02+LPS, in which there is an endpoint (lesser concentration of endotoxin needed to obtain a positive result) already at an ½ dilution.

The biological tests performed with Par37 molecule were carried out by using a synthetic peptide (PEPCHEM, USA).

EXAMPLE 2

IFN-γ Cytokine Release (IFN-γ) cytokine production in supernatants after stimulation with the various antigens was evaluated by ELISA, using commercial kits and following the manufacturers' (GE healthcare, IFNg, Human, Biotrak) instructions. In particular, the data reported in FIG. 4 describe the amount of IFN-γ released by peripheral blood cells of humans in response to stimulation with bacterial LPS. In both subjects studied, LPS pre-incubation with Par37 peptide results in a reduction of cytokine release. Moreover, the experiment reported in FIG. 8 demonstrates that the Par37 peptide is not capable, on itself, of inducing IFN-γ release from peripheral blood cells of 4 human subjects.

EXAMPLE 3

Cytotoxicity Test with HeLa Cells

The cytotoxity tests were carried out on HeLa cell lines growing in adhesion. Cell lines were maintained in RPMI 1640 culture medium containing 10% fetal calf serum and 0.1% antibiotics (penicillin, streptomycin and gentamycin); cultivated under humid 5% $CO_2$ atmosphere at 37° C. To carry out the cytotoxicity test, the system CellTiter 96 AQueous One Solution Cell Proliferation Assay by Promega was used. In short, Hela cells were resuspended in a 100 μl volume of medium at a concentration of 10,000 cells/ml, then seeded on 96-well flat bottom plates and left to adhere in incubator at 37° C. for 3 h. Thereafter, Par37 peptide was added at increasing concentrations (0.5-5-50 μg/ml). The plate was incubated at 37° C. in 5% CO2 for further 48 h. Then 20 μl of CellTiter 96 AQueous One Solution reagent were added. Cells were thus incubated for 1 h at 37° C. in a $CO_2$ incubator. The test was carried out in triplicate and compared to a row of blanks containing exclusively culture medium. After incubation, a spectrophotometer reading was carried out, measuring absorbance at 490 nm. The data are reported in FIG. 5, where it is highlighted that increasing concentrations of Par37 peptide induce no toxic effect on human cells in culture.

EXAMPLE 4

Hemolysis Test

For the hemolysis test, peripheral blood, collected from a donor, in heparin was used. A solution of 6% human erythrocytes was prepared. Erythrocyte concentration was controlled by reading the optical density of an hemolysate of the cell suspension thus made: 0.5 ml blood+7 ml distilled water should give a reading of 0.7 O.D. at the spectrophotometer at 541 nm. Erythrocytes were incubated in triplicate with an increasing concentration of Par37 (0.0025-0.025-0.25-2.5-25 mM) and with 1×PBS as negative control and a 0.1% solution of Triton X100 as positive control. Sample reading was carried out at 415 nm. The data reported in FIG. 6 demonstrate that Par37 peptide, used at different concentrations, has no hemolytic effect on human erythrocytes.

EXAMPLE 5

Histamine Release

The histamine release assay was carried out by using heparinised blood from Pj allergic subjects (n=5) and an allergen concentration scale ranging from 0.0001 and 1 μg/ml. Release protocol was carried out as previously described (Colombo, P., et al., Identification of an immunodominant IgE epitope of the *Parietaria Judaica* major allergen. J. Immunol, 1998. 160(6): p. 2780-5). The data reported in FIG. 9 show the percentage of release obtained after stimulation with Parj1 allergen. On the other hand, when the blood of the same subjects is stimulated with comparable amounts of Par37 peptide no histamine release is observed. Therefore, it can be stated that this peptide exhibits no anaphylactic ability.

EXAMPLE 6

Study of Par37-Induced Cell Proliferation

PBMC from Pj allergic patients (n=3) and non-allergic subjects (n=3) were purified by Ficoll gradient and resuspended in complete RPMI (10% AB serum). Cells were stimulated 5 days with 0.1, 1 and 10 μg/ml rParj1 and Par37. For the determination of stimulation indexes, cells were treated according to what described in the Cell Proliferation ELISA kit, BrdU (colorimetric) (Roche). The results shown in FIG. 7 demonstrate that Parj1 is capable of inducing cell proliferation in all allergic patients; on the other hand, Par37 peptide shows no lymphoproliferative activity in all subjects analyzed.

It should be understood that the embodiments of the present invention are not to be considered as limited to specific composition or biological systems described in the examples, all functionally equivalent peptides and tools being also suitable for the present invention. Unless otherwise described, all technical and scientific terms used in the present description have the same meaning usually understood by a person skilled in the art, to which the description pertains.

The entire description of each document cited in the application is meant to be included in the present invention by reference.

SEQUENCE LISTING

```
                                              SEQ ID NO 1
AntiLPS 1
1                                                       37
LPVSLXHGPVTGPSDPAHKARLERPQIRVPPPAPEKA
X_6 = K or R or H SEQ ID NO 2
AntiLPS 2
1                                                       37
LPVSLRXGPVTGPSDPAHKARLERPQIRVPPPAPEKA
X_7 = K or R or H SEQ ID NO 3
AntiLPS 3
1                                                       37
LPVSLRHGPVTGPSDPAXKARLERPQIRVPPPAPEKA
X_18 = K or R or H SEQ ID NO 4
AntiLPS 4
1                                                       37
LPVSLRHGPVTGPSDPAHXARLERPQIRVPPPAPEKA
X_19 = K or R or H SEQ ID NO 5
AntiLPS 5
1                                                       37
LPVSLRHGPVTGPSDPAHKAXLERPQIRVPPPAPEKA
X_21 = K or R or H SEQ ID NO 6
AntiLPS 6
1                                                       37
LPVSLRHGPVTGPSDPAHKARLEXPQIRVPPPAPEKA
X_24 = K or R or H SEQ ID NO 7
AntiLPS 7
1                                                       37
LPVSLRHGPVTGPSDPAHKARLERPQIRVPPPAPEXA
X_36 = K or R or H SEQ ID NO 8
AntiLPS 8
1                                                       37
XPVSLRHGPVTGPSDPAHKARLERPQIRVPPPAPEKA
X_1 = I or V or L or A SEQ ID NO 9
AntiLPS 9
1                                                       37
LPXSLRHGPVTGPSDPAHKARLERPQIRVPPPAPEKA
X_3 = I or V SEQ ID NO 10
AntiLPS 10
1                                                       37
LPVSXRHGPVTGPSDPAHKARLERPQIRVPPPAPEKA
X_5 = L or A SEQ ID NO 11
AntiLPS 11
1                                                       37
LPVSLRHGPXTGPSDPAHKARLERPQIRVPPPAPEKA
X_10 = I or V or A or L SEQ ID NO 12
AntiLPS 12
1                                                       37
LPVSLRHGPVTGPSDPXHKARLERPQIRVPPPAPEKA
X_17 = I or V or L or A SEQ ID NO 13
AntiLPS 13
1                                                       37
LPVSLRHGPVTGPSDPAHKARLERPQXRVPPPAPEKA
X_27 = I or V or L or A SEQ ID NO 14
AntiLPS 14
1                                                       37
LPVSLRHGPVTGPSDPAHKARLERPQIRXPPPAPEKA
X_29 = I or V or L
```

```
AntiLPS 15
1                                        37
LPVSLRHGPVTGPSDPAHKARLERPQIRVPPPXPEKA
X33 = V or L or A
```
SEQ ID NO 15

```
AntiLPS 16
1                                        37
LPVSLRHGPVTGPSDPAHKARLERPQIRVPPPAPEKX
X37 = I or V or L or A
```
SEQ ID NO 16

```
AntiLPS 17
1                                        37
LPVXLRHGPVTGPSDPAHKARLERPQIRVPPPAPEKA
X4 = G or E or N or S or T or Y
```
SEQ ID NO 17

```
AntiLPS 18
1                                        37
LPVSLRHXPVTGPSDPAHKARLERPQIRVPPPAPEKA
X8 = G or E or N or S or T or Y
```
SEQ ID NO 18

```
AntiLPS 19
1                                        37
LPVSLRHGPVXGPSDPAHKARLERPQIRVPPPAPEKA
X11 = G or E or N or S or T or Y or Q
```
SEQ ID NO 19

```
AntiLPS 20
1                                        37
LPVSLRHGPVTXPSDPAHKARLERPQIRVPPPAPEKA
X12 = G or E or N or S or T or Q
```
SEQ ID NO 20

```
AntiLPS 21
1                                        37
LPVSLKKGPVTGPSDPAHKARLERPQIRVPPPAPEKA
```
SEQ ID NO 21

```
AntiLPS 22
1                                        37
LPVSLRKGPVTGPSDPAKHARLERPQIRVPPPAPEKA
```
SEQ ID NO 22

```
AntiLPS 23
1                                        37
LPVSLRKGPVTGPSDPAHKARLEHPQIKVPPPAPEKA
```
SEQ ID NO 23

```
AntiLPS 24
1                                        37
LPVSLKKGPVTGPSDPAHKARLERPQIRVPPPAPERA
```
SEQ ID NO 24

```
AntiLPS 25
1                                        37
LPVSLHHGPVTGPSDPAHKARLERPQIRVPPPAPEHA
```
SEQ ID NO 25

```
AntiLPS 26
1                                        37
LPISIRHGPVTGPSDPAHKARLERPQIRVPPPAPEKA
```
SEQ ID NO 26

```
AntiLPS 27
1                                        37
LPASVRHGPVTGPSDPAHKARLERPQIRVPPPAPEKA
```
SEQ ID NO 27

```
AntiLPS 28
1                                        37
LPVSLRHGPVTGPSDPAHKLRIERPQIRVPPPAPEKA
```
SEQ ID NO 28

```
AntiLPS 29
1                                        37
LPVSLRHGPVTGPSDPAHKIRVERPQIRVPPPAPEKA
```
SEQ ID NO 29

```
AntiLPS 30
1                                        37
LPVSLRHGPVTGPSDPAHKVRAERPQIRVPPPAPEKA
```
SEQ ID NO 30

```
AntiLPS 31
1                                        37
LPVSLRHGPVTGPSDPAHKARLERPQIRAPPPIPEKA
```
SEQ ID NO 31

```
AntiLPS 32
LPVSLRHGPVTGPSD (deletion 16-37)
```
SEQ ID NO 32

```
AntiLPS 33
PAHKARLERPQIRVPPPAPEKA (deletion 1-15)
```
SEQ ID NO 33

```
AntiLPS 34
HGPVTGPSDPAHKARLERPQI (deletion 1-6 and 28-37)
```
SEQ ID NO 34

```
AntiLPS 35
TGPSDPAHKARLERPQIRVPPP (deletion 1-10 and 33-37)
```
SEQ ID NO 35

```
AntiLPS 36
LPVSLRHGPVTGPSDIRVPPPAPEKA (deletion 16-26)
```
SEQ ID NO 36

```
AntiLPS 37
LERPQIRVPPPAPEKA (deletion 1-21)
```
SEQ ID NO 37

```
AntiLPS 38
QETCGTMVRALMPCLPFVQGKEKEPSKGCCSGAKRLDGETKTGPQRVHAC
ECIQTAMKTYSDIDGKLVSEVPKHCGIVDSKLPPIDVNMDCKTVGVVPRQ
PQLPVSLRHGPVTG
139
PSDPAHKARLERPQIRVPPPAPEKA
P43217/NLT11_ParJ1.01
```
SEQ ID NO 38

```
AntiLPS 39
QETCGTMVRALMPCLPFVQGKEKEPSKGCCSGAKRLDGETKTGPQRVHAC
ECIQTAMKTYSDIDGKLVSEVPKHCGIVDSKLPPIDVNMDCKTVGVVPRQ
PQLPVSLRHGPVTGPSDPAHKARLE
fused peptide 125 aa
```
SEQ ID NO 39

```
AntiLPS 40
1                                          40
MRGSHHHHHHGSLPVSLRHGPVTGPSDPAHKARLERPQIRVPPPAPEKA
fusion peptide 49 aa
```
SEQ ID NO 40

```
AntiLPS 41
1                                        37
LPVSLRHGPVTGPSDPAHKARLERPQIRVPPPAPEKA
Wild type C-terminal peptide
```
SEQ ID NO 41

```
AntiLPS 42
EEACGKVVQDIMPCLHFVKGEEKEPSKECCSGTKKLSEEVKTTEQKREAC
KCIVRATKGISGIKNELVAEVPKKCDIKTT-LPPITADFDCSKIQSTIFR
GYY
Parj1.02
```
SEQ ID NO 42

The invention claimed is:

1. An isolated peptide capable of binding and/or neutralizing biological activity of bacterial membrane lipopolysaccharide (LPS) endotoxin, said peptide consisting of the amino acid sequence

[X'-(aa)$_n$-X'']$_m$ wherein 'aa' means LPVSLRHGPVTGPSDPAHKARLERPQIRVPPPAPEKA (SEQ ID NO: 41), m is an integer from 1 to 100, a region (aa)$_n$ has a total net positive charge and is obtained by substitution of any amino acid residue in SEQ ID NO: 41 by another amino acid residue having equivalent charge characteristics or by deletion of up to 27 residues, and X' and X'' are each independently a linear peptide from 0 to 4 amino acid residues.

2. An isolated and cyclic peptide capable of binding and/or neutralizing biological activity of bacterial membrane lipopolysaccharide (LPS) endotoxin, said peptide consisting of the amino acid sequence

[X'-(aa)$_n$-X'']$_m$ which is modified to obtain a cyclic configuration, wherein 'aa' means LPVSLRHGPVTGPSDPAHKARLERPQIRVPPPAPEKA (SEQ ID NO: 41), m is an integer from 1 to 100, (aa)$_n$ has a total net positive charge and is obtained by substitution of any amino acid residue in SEQ ID NO: 41 by another amino acid residue having equivalent charge characteristics or by deletion of up to 27 residues, X' and X'' are each independently a linear peptide from 0 to 4 amino acid residues.

3. The peptide according to claim 1, which is a hybrid protein comprising the region (aa)$_n$ and a heterologous protein, wherein the region (aa)$_n$ is at the amino-terminal end of, or at the carboxy-terminal end of, or inserted inside the heterologous protein.

4. The peptide according to claim 1, wherein m is an integer from 2 to 100.

5. A method of treatment or diagnosis comprising binding bacterial membrane lipopolysaccharide (LPS) endotoxin and/or neutralizing its biological activity using the peptide according to claim 1.

6. The method according to claim 5 for treatment or diagnosis of at least of septic shock or inflammatory reactions.

7. The method according to claim 6, wherein the peptide is used as an immunosuppressive adjuvant in therapy.

8. A composition comprising a peptide according to claim 1 and at least a pharmaceutically acceptable excipient, adjuvant, or diluent.

9. The pharmaceutical composition according to claim 8 in the form of solution, suspension, emulsion, cream, ointment, or implant for parenteral, subcutaneous, intramuscular, intravenous, topical, oral administration, or subcutaneous implantation.

10. A method of preparation of a pharmaceutical composition comprising mixing a pharmaceutically active amount of the peptide according to claim 1 with at least a pharmaceutically acceptable excipient, adjuvant, or diluent.

11. A medical device comprising the peptide according to claim 1 for use in at least binding, removing, or deactivating bacterial membrane lipopolysaccharide (LPS) endotoxin.

12. The medical device of claim 11, wherein the peptide is comprised in a purifying unit suitable for extra-corporal treatment of body fluid.

13. An in vitro or in vivo method for interfering and/or minimizing the biological effects associated with presence of bacterial membrane lipopolysaccharide (LPS) endotoxin in a liquid or a biological material, the method comprising binding LPS endotoxin present in the liquid or the biological material to the peptide according to claim 1.

14. The peptide according to claim 1, wherein X' and X" consists of 0 amino acid residues.

15. The peptide according to claim 1, wherein X' consists of 1 or 2 amino acid residues.

16. The peptide according to claim 1, wherein X" consists of 1 or 2 amino acid residues.

17. The peptide according to claim 1, wherein m is an integer from 2 to 5.

18. The peptide according to claim 1, wherein m is an integer from 2 to 10.

19. The peptide according to claim 1, wherein m is an integer from 2 to 20.

20. The peptide according to claim 1, wherein the region $(aa)_n$ is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, and SEQ ID NO: 37.

* * * * *

UNITED STATES PATENT AND TRADEMARK OFFICE
CERTIFICATE OF CORRECTION

PATENT NO.        : 8,535,680 B2                     Page 1 of 1
APPLICATION NO.   : 12/933390
DATED             : September 17, 2013
INVENTOR(S)       : Colombo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 42

<210> SEQ ID NO 1
<211> LENGTH: 37
<212> TYPE: PRT
<213> ORGANISM: Parietaria sp.
<220> FEATURE:
<221> NAME/KEY: MISC_FEATURE
<222> LOCATION: (6)..(6)
<223> OTHER INFORMATION: Xaa = K or R or H

<400> SEQUENCE: 1

Leu Pro Val Ser Leu Xaa His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 2
<211> LENGTH: 37
<212> TYPE: PRT
<213> ORGANISM: Parietaria sp.
<221> NAME/KEY: MISC_FEATURE
<222> LOCATION: (7)..(7)
<223> OTHER INFORMATION: Xaa = K or R or H

<400> SEQUENCE: 2

Leu Pro Val Ser Leu Arg Xaa Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 3
<211> LENGTH: 37
<212> TYPE: PRT
<213> ORGANISM: Parietaria sp.
<220> FEATURE:
<221> NAME/KEY: MISC_FEATURE
<222> LOCATION: (18)..(18)
<223> OTHER INFORMATION: Xaa = K or R or H

<400> SEQUENCE: 3

Leu Pro Val Ser Leu Arg His Gly Pro Val Thr Gly Pro Ser Asp Pro
1               5                   10                  15

Ala Xaa Lys Ala Arg Leu Glu Arg Pro Gln Ile Arg Val Pro Pro Pro
            20                  25                  30

Ala Pro Glu Lys Ala
        35

<210> SEQ ID NO 4
<211> LENGTH: 37
<212> TYPE: PRT
<213> ORGANISM: Parietaria sp.
<220> FEATURE:
<221> NAME/KEY: MISC_FEATURE
<222> LOCATION: (19)..(19)
<223> OTHER INFORMATION: Xaa = K or R or H

<400> SEQUENCE: 4

Leu Pro Val Ser Leu Arg His Gly Pro Val Thr Gly Pro Ser Asp Pro
1               5                   10                  15

```
Ala His Xaa Ala Arg Leu Glu Arg Pro Gln Ile Arg Val Pro Pro Pro
            20                  25                  30

Ala Pro Glu Lys Ala
        35

<210> SEQ ID NO 5
<211> LENGTH: 37
<212> TYPE: PRT
<213> ORGANISM: Parietaria sp.
<220> FEATURE:
<221> NAME/KEY: MISC_FEATURE
<222> LOCATION: (21)..(21)
<223> OTHER INFORMATION: Xaa = K or R or H

<400> SEQUENCE: 5

Leu Pro Val Ser Leu Arg His Gly Pro Val Thr Gly Pro Ser Asp Pro
1               5                   10                  15

Ala His Lys Ala Xaa Leu Glu Arg Pro Gln Ile Arg Val Pro Pro Pro
            20                  25                  30

Ala Pro Glu Lys Ala
        35

<210> SEQ ID NO 6
<211> LENGTH: 37
<212> TYPE: PRT
<213> ORGANISM: Parietaria sp.
<220> FEATURE:
<221> NAME/KEY: MISC_FEATURE
<222> LOCATION: (24)..(24)
<223> OTHER INFORMATION: Xaa = K or R or H

<400> SEQUENCE: 6

Leu Pro Val Ser Leu Arg His Gly Pro Val Thr Gly Pro Ser Asp Pro
1               5                   10                  15

Ala His Lys Ala Arg Leu Glu Xaa Pro Gln Ile Arg Val Pro Pro Pro
            20                  25                  30

Ala Pro Glu Lys Ala
        35

<210> SEQ ID NO 7
<211> LENGTH: 37
<212> TYPE: PRT
<213> ORGANISM: Parietaria sp.
<220> FEATURE:
<221> NAME/KEY: MISC_FEATURE
<222> LOCATION: (36)..(36)
<223> OTHER INFORMATION: Xaa = K or R or H

<400> SEQUENCE: 7

Leu Pro Val Ser Leu Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Xaa Ala
        35

<210> SEQ ID NO 8
<211> LENGTH: 37
<212> TYPE: PRT
<213> ORGANISM: Parietaria sp.
<220> FEATURE:
<221> NAME/KEY: MISC_FEATURE
<222> LOCATION: (1)..(1)
<223> OTHER INFORMATION: Xaa = I or V or L or A
```

-continued

```
<400> SEQUENCE: 8

Xaa Pro Val Ser Leu Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 9
<211> LENGTH: 37
<212> TYPE: PRT
<213> ORGANISM: Parietaria sp.
<220> FEATURE:
<221> NAME/KEY: MISC_FEATURE
<222> LOCATION: (3)..(3)
<223> OTHER INFORMATION: Xaa = I or V

<400> SEQUENCE: 9

Leu Pro Xaa Ser Leu Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 10
<211> LENGTH: 37
<212> TYPE: PRT
<213> ORGANISM: Parietaria sp.
<220> FEATURE:
<221> NAME/KEY: MISC_FEATURE
<222> LOCATION: (5)..(5)
<223> OTHER INFORMATION: Xaa = L or A

<400> SEQUENCE: 10

Leu Pro Val Ser Xaa Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 11
<211> LENGTH: 37
<212> TYPE: PRT
<213> ORGANISM: Parietaria sp.
<220> FEATURE:
<221> NAME/KEY: MISC_FEATURE
<222> LOCATION: (10)..(10)
<223> OTHER INFORMATION: Xaa = I or V or A or L

<400> SEQUENCE: 11

Leu Pro Val Ser Leu Arg His Gly Pro Xaa Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 12
<211> LENGTH: 37
<212> TYPE: PRT
<213> ORGANISM: Parietaria sp.
<220> FEATURE:
```

```
<221> NAME/KEY: MISC_FEATURE
<222> LOCATION: (17)..(17)
<223> OTHER INFORMATION: Xaa = I or V or L or A

<400> SEQUENCE: 12

Leu Pro Val Ser Leu Arg His Gly Pro Val Thr Gly Pro Ser Asp Pro
1               5                   10                  15

Xaa His Lys Ala Arg Leu Glu Arg Pro Gln Ile Arg Val Pro Pro Pro
            20                  25                  30

Ala Pro Glu Lys Ala
        35

<210> SEQ ID NO 13
<211> LENGTH: 37
<212> TYPE: PRT
<213> ORGANISM: Parietaria sp.
<220> FEATURE:
<221> NAME/KEY: MISC_FEATURE
<222> LOCATION: (27)..(27)
<223> OTHER INFORMATION: Xaa = I or V or L or A

<400> SEQUENCE: 13

Leu Pro Val Ser Leu Arg His Gly Pro Val Thr Gly Pro Ser Asp Pro
1               5                   10                  15

Ala His Lys Ala Arg Leu Glu Arg Pro Gln Xaa Arg Val Pro Pro Pro
            20                  25                  30

Ala Pro Glu Lys Ala
        35

<210> SEQ ID NO 14
<211> LENGTH: 37
<212> TYPE: PRT
<213> ORGANISM: Parietaria sp.
<220> FEATURE:
<221> NAME/KEY: MISC_FEATURE
<222> LOCATION: (29)..(29)
<223> OTHER INFORMATION: Xaa = I or V or L

<400> SEQUENCE: 14

Leu Pro Val Ser Leu Arg His Gly Pro Val Thr Gly Pro Ser Asp Pro
1               5                   10                  15

Ala His Lys Ala Arg Leu Glu Arg Pro Gln Ile Arg Xaa Pro Pro Pro
            20                  25                  30

Ala Pro Glu Lys Ala
        35

<210> SEQ ID NO 15
<211> LENGTH: 37
<212> TYPE: PRT
<213> ORGANISM: Parietaria sp.
<220> FEATURE:
<221> NAME/KEY: MISC_FEATURE
<222> LOCATION: (33)..(33)
<223> OTHER INFORMATION: Xaa = V or L or A

<400> SEQUENCE: 15

Leu Pro Val Ser Leu Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Xaa Pro Glu Lys Ala
        35

<210> SEQ ID NO 16
```

```
<211> LENGTH: 37
<212> TYPE: PRT
<213> ORGANISM: Parietaria sp.
<220> FEATURE:
<221> NAME/KEY: MISC_FEATURE
<222> LOCATION: (37)..(37)
<223> OTHER INFORMATION: Xaa = I or V or L or A

<400> SEQUENCE: 16

Leu Pro Val Ser Leu Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Xaa
        35

<210> SEQ ID NO 17
<211> LENGTH: 37
<212> TYPE: PRT
<213> ORGANISM: Parietaria sp.
<220> FEATURE:
<221> NAME/KEY: MISC_FEATURE
<222> LOCATION: (4)..(4)
<223> OTHER INFORMATION: Xaa = G or E or N or S or T or Y

<400> SEQUENCE: 17

Leu Pro Val Xaa Leu Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 18
<211> LENGTH: 37
<212> TYPE: PRT
<213> ORGANISM: Parietaria sp.
<220> FEATURE:
<221> NAME/KEY: MISC_FEATURE
<222> LOCATION: (8)..(8)
<223> OTHER INFORMATION: Xaa= G or E or N or S or T or Y

<400> SEQUENCE: 18

Leu Pro Val Ser Leu Arg His Xaa Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 19
<211> LENGTH: 37
<212> TYPE: PRT
<213> ORGANISM: Parietaria sp.
<220> FEATURE:
<221> NAME/KEY: MISC_FEATURE
<222> LOCATION: (11)..(11)
<223> OTHER INFORMATION: Xaa = G or E or N or S or T or Y or Q

<400> SEQUENCE: 19

Leu Pro Val Ser Leu Arg His Gly Pro Val Xaa Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
```

<210> SEQ ID NO 20
<211> LENGTH: 37
<212> TYPE: PRT
<213> ORGANISM: Parietaria sp.
<220> FEATURE:
<221> NAME/KEY: MISC_FEATURE
<222> LOCATION: (12)..(12)
<223> OTHER INFORMATION: Xaa = G or E or N or S or T or Q

<400> SEQUENCE: 20

Leu Pro Val Ser Leu Arg His Gly Pro Val Thr Xaa Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 21
<211> LENGTH: 37
<212> TYPE: PRT
<213> ORGANISM: Parietaria sp.

<400> SEQUENCE: 21

Leu Pro Val Ser Leu Lys Lys Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 22
<211> LENGTH: 37
<212> TYPE: PRT
<213> ORGANISM: Parietaria sp.

<400> SEQUENCE: 22

Leu Pro Val Ser Leu Arg Lys Gly Pro Val Thr Gly Pro Ser Asp Pro
1               5                   10                  15

Ala Lys His Ala Arg Leu Glu Arg Pro Gln Ile Arg Val Pro Pro Pro
            20                  25                  30

Ala Pro Glu Lys Ala
        35

<210> SEQ ID NO 23
<211> LENGTH: 37
<212> TYPE: PRT
<213> ORGANISM: Parietaria sp.

<400> SEQUENCE: 23

Leu Pro Val Ser Leu Arg Lys Gly Pro Val Thr Gly Pro Ser Asp Pro
1               5                   10                  15

Ala His Lys Ala Arg Leu Glu His Pro Gln Ile Lys Val Pro Pro Pro
            20                  25                  30

Ala Pro Glu Lys Ala
        35

<210> SEQ ID NO 24
<211> LENGTH: 37
<212> TYPE: PRT
<213> ORGANISM: Parietaria sp.

-continued

```
<400> SEQUENCE: 24

Leu Pro Val Ser Leu Lys Lys Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Arg Ala
        35

<210> SEQ ID NO 25
<211> LENGTH: 37
<212> TYPE: PRT
<213> ORGANISM: Parietaria sp.

<400> SEQUENCE: 25

Leu Pro Val Ser Leu His His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu His Ala
        35

<210> SEQ ID NO 26
<211> LENGTH: 37
<212> TYPE: PRT
<213> ORGANISM: Parietaria sp.

<400> SEQUENCE: 26

Leu Pro Ile Ser Ile Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 27
<211> LENGTH: 37
<212> TYPE: PRT
<213> ORGANISM: Parietaria sp.

<400> SEQUENCE: 27

Leu Pro Ala Ser Val Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 28
<211> LENGTH: 37
<212> TYPE: PRT
<213> ORGANISM: Parietaria sp.

<400> SEQUENCE: 28

Leu Pro Val Ser Leu Arg His Gly Pro Val Thr Gly Pro Ser Asp Pro
1               5                   10                  15

Ala His Lys Leu Arg Ile Glu Arg Pro Gln Ile Arg Val Pro Pro Pro
            20                  25                  30

Ala Pro Glu Lys Ala
        35
```

```
<210> SEQ ID NO 29
<211> LENGTH: 37
<212> TYPE: PRT
<213> ORGANISM: Parietaria sp.

<400> SEQUENCE: 29

Leu Pro Val Ser Leu Arg His Gly Pro Val Thr Gly Pro Ser Asp Pro
1               5                   10                  15

Ala His Lys Ile Arg Val Glu Arg Pro Gln Ile Arg Val Pro Pro Pro
            20                  25                  30

Ala Pro Glu Lys Ala
        35

<210> SEQ ID NO 30
<211> LENGTH: 37
<212> TYPE: PRT
<213> ORGANISM: Parietaria sp.

<400> SEQUENCE: 30

Leu Pro Val Ser Leu Arg His Gly Pro Val Thr Gly Pro Ser Asp Pro
1               5                   10                  15

Ala His Lys Val Arg Ala Glu Arg Pro Gln Ile Arg Val Pro Pro Pro
            20                  25                  30

Ala Pro Glu Lys Ala
        35

<210> SEQ ID NO 31
<211> LENGTH: 37
<212> TYPE: PRT
<213> ORGANISM: Parietaria sp.

<400> SEQUENCE: 31

Leu Pro Val Ser Leu Arg His Gly Pro Val Thr Gly Pro Ser Asp Pro
1               5                   10                  15

Ala His Lys Ala Arg Leu Glu Arg Pro Gln Ile Arg Ala Pro Pro Pro
            20                  25                  30

Ile Pro Glu Lys Ala
        35

<210> SEQ ID NO 32
<211> LENGTH: 15
<212> TYPE: PRT
<213> ORGANISM: Parietaria sp.
<220> FEATURE:
<221> NAME/KEY: MISC_FEATURE
<222> LOCATION: (16)..(37)
<223> OTHER INFORMATION: deletion from position 16 to position 37 of
      wild type peptide (SEQ ID NO 41)

<400> SEQUENCE: 32

Leu Pro Val Ser Leu Arg His Gly Pro Val Thr Gly Pro Ser Asp
1               5                   10                  15

<210> SEQ ID NO 33
<211> LENGTH: 22
<212> TYPE: PRT
<213> ORGANISM: Parietaria sp.
<220> FEATURE:
<221> NAME/KEY: MISC_FEATURE
<222> LOCATION: (1)..(15)
<223> OTHER INFORMATION: deletion from position 1 to position 15 of wild
      type peptide (SEQ ID NO 41)

<400> SEQUENCE: 33

Pro Ala His Lys Ala Arg Leu Glu Arg Pro Gln Ile Arg Val Pro Pro
```

-continued

```
                1               5                  10                 15
Pro Ala Pro Glu Lys Ala
            20

<210> SEQ ID NO 34
<211> LENGTH: 21
<212> TYPE: PRT
<213> ORGANISM: Parietaria sp.
<220> FEATURE:
<221> NAME/KEY: MISC_FEATURE
<223> OTHER INFORMATION: deletion from position 1 to position 6 and from
      position 28 to position 37 of wild type peptide (SEQ ID NO 41)

<400> SEQUENCE: 34

His Gly Pro Val Thr Gly Pro Ser Asp Pro Ala His Lys Ala Arg Leu
1               5                   10                  15

Glu Arg Pro Gln Ile
            20

<210> SEQ ID NO 35
<211> LENGTH: 22
<212> TYPE: PRT
<213> ORGANISM: Parietaria sp.
<220> FEATURE:
<221> NAME/KEY: MISC_FEATURE
<223> OTHER INFORMATION: deletion from position 1 to position 10 and
      from position 33 to position 37 of wild type peptide
      (SEQ ID NO 41)

<400> SEQUENCE: 35

Thr Gly Pro Ser Asp Pro Ala His Lys Ala Arg Leu Glu Arg Pro Gln
1               5                   10                  15

Ile Arg Val Pro Pro Pro
            20

<210> SEQ ID NO 36
<211> LENGTH: 26
<212> TYPE: PRT
<213> ORGANISM: Parietaria sp.
<220> FEATURE:
<221> NAME/KEY: MISC_FEATURE
<222> LOCATION: (16)..(26)
<223> OTHER INFORMATION: deletion from position 16 to position 26 of
      wild type peptide (SEQ ID NO 41)

<400> SEQUENCE: 36

Leu Pro Val Ser Leu Arg His Gly Pro Val Thr Gly Pro Ser Asp Ile
1               5                   10                  15

Arg Val Pro Pro Pro Ala Pro Glu Lys Ala
            20                  25

<210> SEQ ID NO 37
<211> LENGTH: 16
<212> TYPE: PRT
<213> ORGANISM: Parietaria sp.
<220> FEATURE:
<221> NAME/KEY: MISC_FEATURE
<223> OTHER INFORMATION: deletion from position 1 to position 21 of
      wild type peptide (SEQ ID NO 41)

<400> SEQUENCE: 37

Leu Glu Arg Pro Gln Ile Arg Val Pro Pro Pro Ala Pro Glu Lys Ala
1               5                   10                  15

<210> SEQ ID NO 38
<211> LENGTH: 139
<212> TYPE: PRT
```

<210> SEQ ID NO 38
<211> LENGTH: 138
<212> TYPE: PRT
<213> ORGANISM: Parietaria sp.

<400> SEQUENCE: 38

Gln Glu Thr Cys Gly Thr Met Val Arg Ala Leu Met Pro Cys Leu Pro
1               5                   10                  15

Phe Val Gln Gly Lys Glu Lys Glu Pro Ser Lys Gly Cys Cys Ser Gly
            20                  25                  30

Ala Lys Arg Leu Asp Gly Glu Thr Lys Thr Gly Pro Gln Arg Val His
        35                  40                  45

Ala Cys Glu Cys Ile Gln Thr Ala Met Lys Thr Tyr Ser Asp Ile Asp
    50                  55                  60

Gly Lys Leu Val Ser Glu Val Pro Lys His Cys Gly Ile Val Asp Ser
65                  70                  75                  80

Lys Leu Pro Pro Ile Asp Val Asn Met Asp Cys Lys Thr Val Gly Val
                85                  90                  95

Val Pro Arg Gln Pro Gln Leu Pro Val Ser Leu Arg His Gly Pro Val
            100                 105                 110

Thr Gly Pro Ser Asp Pro Ala His Lys Ala Arg Leu Glu Arg Pro Gln
        115                 120                 125

Ile Arg Val Pro Pro Ala Pro Glu Lys Ala
    130                 135

<210> SEQ ID NO 39
<211> LENGTH: 125
<212> TYPE: PRT
<213> ORGANISM: Parietaria sp.

<400> SEQUENCE: 39

Gln Glu Thr Cys Gly Thr Met Val Arg Ala Leu Met Pro Cys Leu Pro
1               5                   10                  15

Phe Val Gln Gly Lys Glu Lys Glu Pro Ser Lys Gly Cys Cys Ser Gly
            20                  25                  30

Ala Lys Arg Leu Asp Gly Glu Thr Lys Thr Gly Pro Gln Arg Val His
        35                  40                  45

Ala Cys Glu Cys Ile Gln Thr Ala Met Lys Thr Tyr Ser Asp Ile Asp
    50                  55                  60

Gly Lys Leu Val Ser Glu Val Pro Lys His Cys Gly Ile Val Asp Ser
65                  70                  75                  80

Lys Leu Pro Pro Ile Asp Val Asn Met Asp Cys Lys Thr Val Gly Val
                85                  90                  95

Val Pro Arg Gln Pro Gln Leu Pro Val Ser Leu Arg His Gly Pro Val
            100                 105                 110

Thr Gly Pro Ser Asp Pro Ala His Lys Ala Arg Leu Glu
        115                 120                 125

<210> SEQ ID NO 40
<211> LENGTH: 49
<212> TYPE: PRT
<213> ORGANISM: Parietaria sp.

<400> SEQUENCE: 40

Met Arg Gly Ser His His His His His His Gly Ser Leu Pro Val Ser
1               5                   10                  15

Leu Arg His Gly Pro Val Thr Gly Pro Ser Asp Pro Ala His Lys Ala
            20                  25                  30

Arg Leu Glu Arg Pro Gln Ile Arg Val Pro Pro Ala Pro Glu Lys
        35                  40                  45

```
Ala

<210> SEQ ID NO 41
<211> LENGTH: 37
<212> TYPE: PRT
<213> ORGANISM: Parietaria sp.

<400> SEQUENCE: 41

Leu Pro Val Ser Leu Arg His Gly Pro Val Thr Gly Pro Ser Asp Pro
1               5                   10                  15

Ala His Lys Ala Arg Leu Glu Arg Pro Gln Ile Arg Val Pro Pro Pro
            20                  25                  30

Ala Pro Glu Lys Ala
        35

<210> SEQ ID NO 42
<211> LENGTH: 102
<212> TYPE: PRT
<213> ORGANISM: Parietaria sp

<400> SEQUENCE: 42

Glu Glu Ala Cys Gly Lys Val Val Gln Asp Ile Met Pro Cys Leu His
1               5                   10                  15

Phe Val Lys Gly Glu Glu Lys Glu Pro Ser Lys Glu Cys Cys Ser Gly
            20                  25                  30

Thr Lys Lys Leu Ser Glu Glu Val Lys Thr Thr Glu Gln Lys Arg Glu
        35                  40                  45

Ala Cys Lys Cys Ile Val Arg Ala Thr Lys Gly Ile Ser Gly Ile Lys
    50                  55                  60

Asn Glu Leu Val Ala Glu Val Pro Lys Lys Cys Asp Ile Lys Thr Thr
65                  70                  75                  80

Leu Pro Pro Ile Thr Ala Asp Phe Asp Cys Ser Lys Ile Gln Ser Thr
                85                  90                  95

Ile Phe Arg Gly Tyr Tyr
            100
```